(12) United States Patent
Zhang et al.

(10) Patent No.: US 9,193,033 B2
(45) Date of Patent: Nov. 24, 2015

(54) METHOD OF IMPROVING BOND STRENGTH OF POLYMERIC IMPLANTS WITH BONE CEMENT

(71) Applicant: Howmedica Osteonics Corp., Mahwah, NJ (US)

(72) Inventors: Zongtao Zhang, Riverdale, NJ (US); Keenan Michael Hanson, Tuxedo, NY (US); Daniel E. Lawrynowicz, Monroe, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 206 days.

(21) Appl. No.: 13/792,421

(22) Filed: Mar. 11, 2013

(65) Prior Publication Data

US 2014/0256229 A1   Sep. 11, 2014

(51) Int. Cl.
*B24C 1/00* (2006.01)
*B24C 1/06* (2006.01)
*A61F 2/30* (2006.01)
*A61F 2/38* (2006.01)

(52) U.S. Cl.
CPC . *B24C 1/003* (2013.01); *A61F 2/30* (2013.01); *A61F 2/30767* (2013.01); *A61F 2/389* (2013.01); *B24C 1/06* (2013.01); *A61F 2002/305* (2013.01); *A61F 2002/30607* (2013.01); *A61F 2002/30906* (2013.01)

(58) Field of Classification Search
CPC ....... B24C 1/003; B24C 1/06; A61F 2/30767; A61F 2002/305; A61F 2002/30607; A61F 2002/30906

USPC .................................................. 451/38, 39, 40
See application file for complete search history.

(56) References Cited

U.S. PATENT DOCUMENTS

| 6,210,445 | B1 * | 4/2001 | Zawadzki | 623/20.33 |
| 7,867,061 | B2 * | 1/2011 | Elshout | 451/40 |
| 8,475,536 | B2 * | 7/2013 | Tong et al. | 623/23.57 |
| 2009/0084491 | A1 * | 4/2009 | Uthgenannt et al. | 156/153 |
| 2010/0100191 | A1 * | 4/2010 | May et al. | 623/20.34 |
| 2010/0249945 | A1 * | 9/2010 | Yakimicki et al. | 623/23.59 |
| 2010/0312348 | A1 * | 12/2010 | Wang et al. | 623/18.11 |
| 2011/0035018 | A1 * | 2/2011 | Deffenbaugh et al. | 623/20.28 |
| 2011/0190902 | A1 * | 8/2011 | Tong et al. | 623/23.5 |
| 2012/0074098 | A1 * | 3/2012 | Nary Filho et al. | 216/53 |

OTHER PUBLICATIONS

Abernethy et al., Fracture of metal tibia tray after kinamatic total knee replacement, a common casuse of early aseptic failure, The Journal of Bone and Joint Surgery, vol. 78-B, No. 2, pp. 220-225, 1996.
Altintas et al., Fracture of the tibial tray after total knee arthroplasty, The Journal of Arthroplasty, vol. 14, No. 1, pp. 112-114, 1999.

(Continued)

*Primary Examiner* — Maurina Rachuba
(74) *Attorney, Agent, or Firm* — Lerner, David, Littenberg, Krumholz & Mentlik, LLP

(57) ABSTRACT

A method for improving the bond between a PEEK joint component and bone cement comprising roughening a surface of the PEEK component by air-blasting abrasive water-soluble particles against the component until an average surface roughness of 4 to 6 micrometers is attained and subsequently submerging the component in water to dissolve any residual particles.

12 Claims, 6 Drawing Sheets

(56) References Cited

OTHER PUBLICATIONS

Brant et al., "Ebeded Erosive particles from the grit-blasting process: a promoter of tibial backside wear." 52nd Annual meeting of the Orthopedic Research Society, Paper No. 0553, 1 page.

Chong et al., The influence of tibial component fixation techniques on resorption of supporting bone stock after total knee replacement, J Biomech., 44(5), pp. 948-954, Mar. 2011.

Khaw et al., A randomised controlled trials of cemented versus cemented press-fit condular total knee replacement, J Bone Joint Surg, 84-B, pp. 658-666, 2002.

Levitz et al., Long-term changes in bone mineral density following total knee replacement, Clin Orthop Relat Res., No. 321, pp. 68-72, 1995.

Petersen et al., Changes in bone mineral density of the proximal tibia after uncemented total knee arthroplasty: a 3-year follow-up of 25 knees, Acta Orthop Scand. 66, 6, pp. 513-516, 1995.

Pittman, et al, "Mechanical bond strength of the cement-tibia component interface in total knee arthroplasty," The Journal of Arthroplasty, vol. 21, No. 6, pp. 883-888, 2006.

Raab et al., The quasistatic and fatigue performance of the implant/bone-cement interface, Journal of Biomedical materials Research, vol. 15, pp. 159-182, 1981.

Ta-Feng Ho et al., Early tibial tray failure of a Duracon Knee with retrieval analysis, The journal of Arthroplasty, vol. 19, No. 6, pp. 797-802, 2004.

Uhmwpe Handbook 2nd edition, Chapter 7, "The origins and Adaptations of UHMWWPE for knee replacement," pp. 81-95, undated.

* cited by examiner

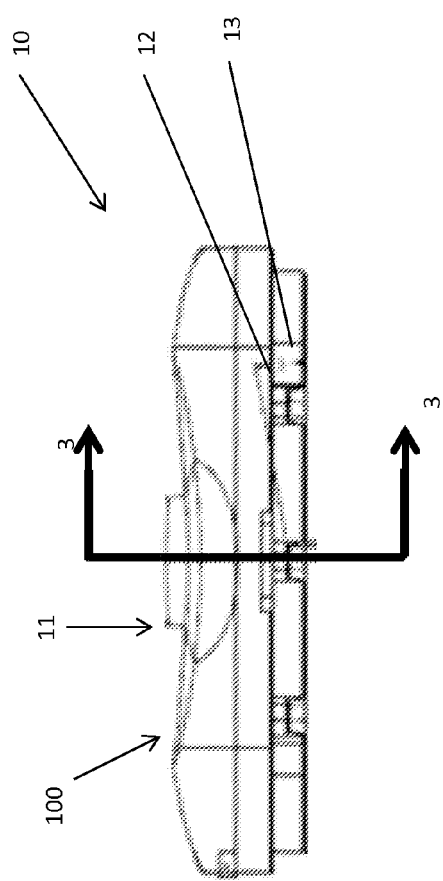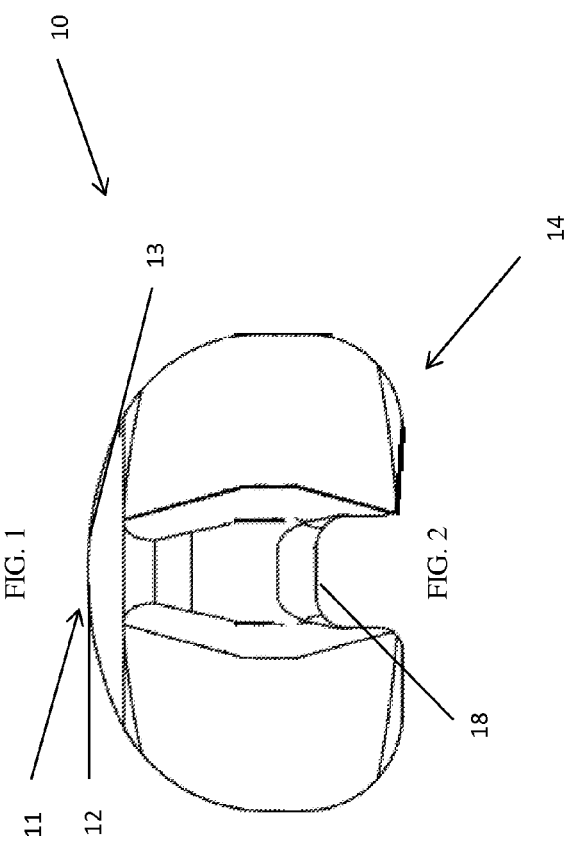

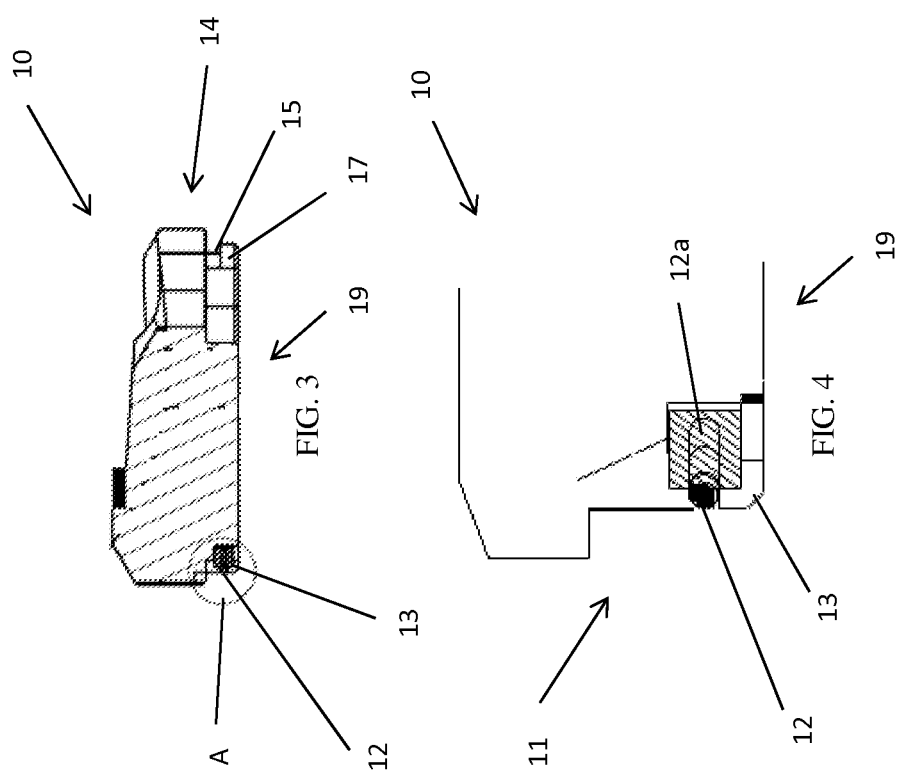

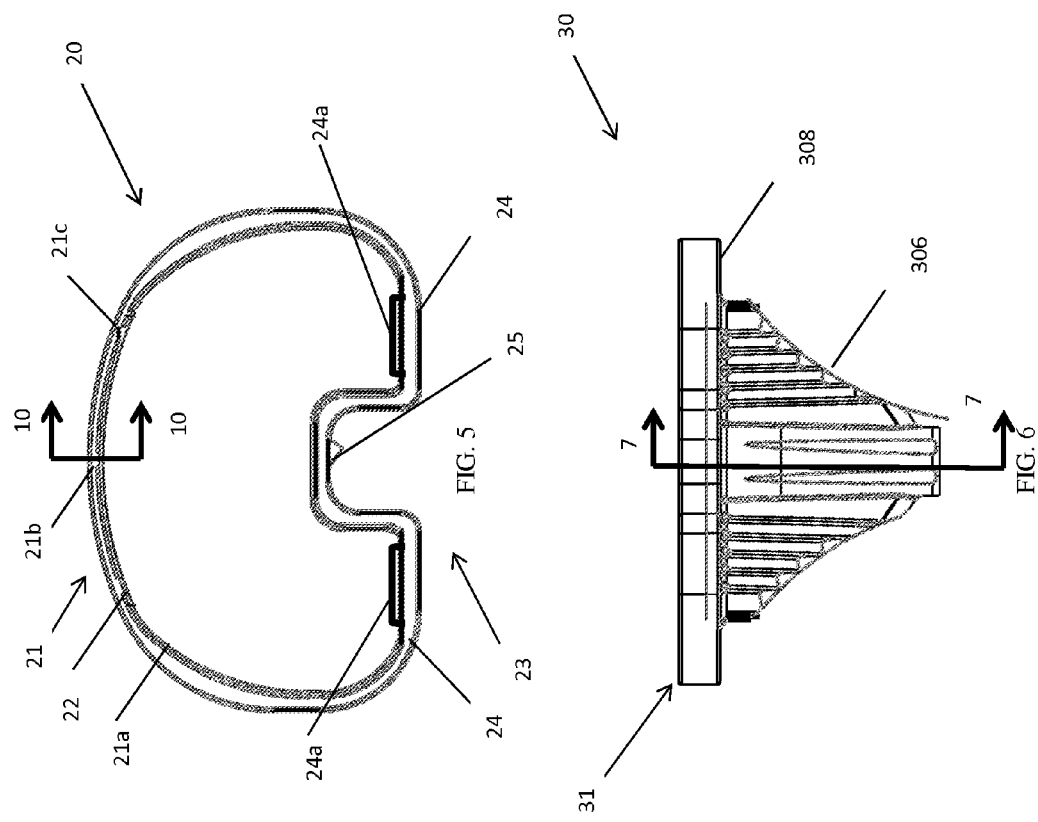

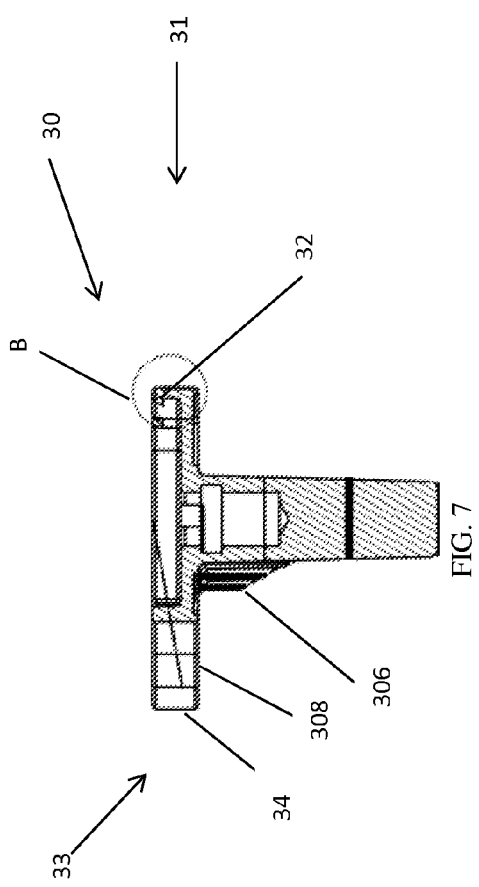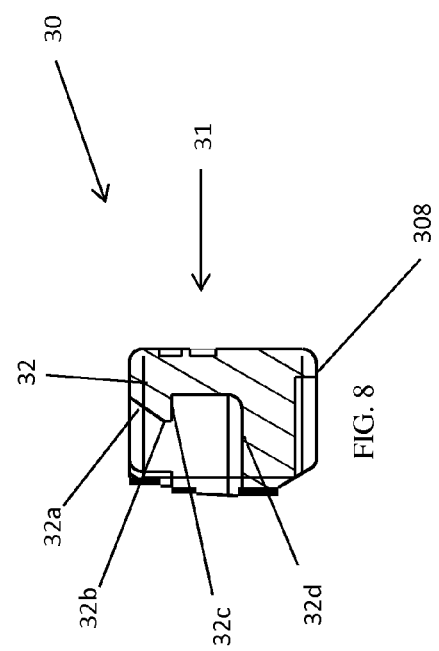

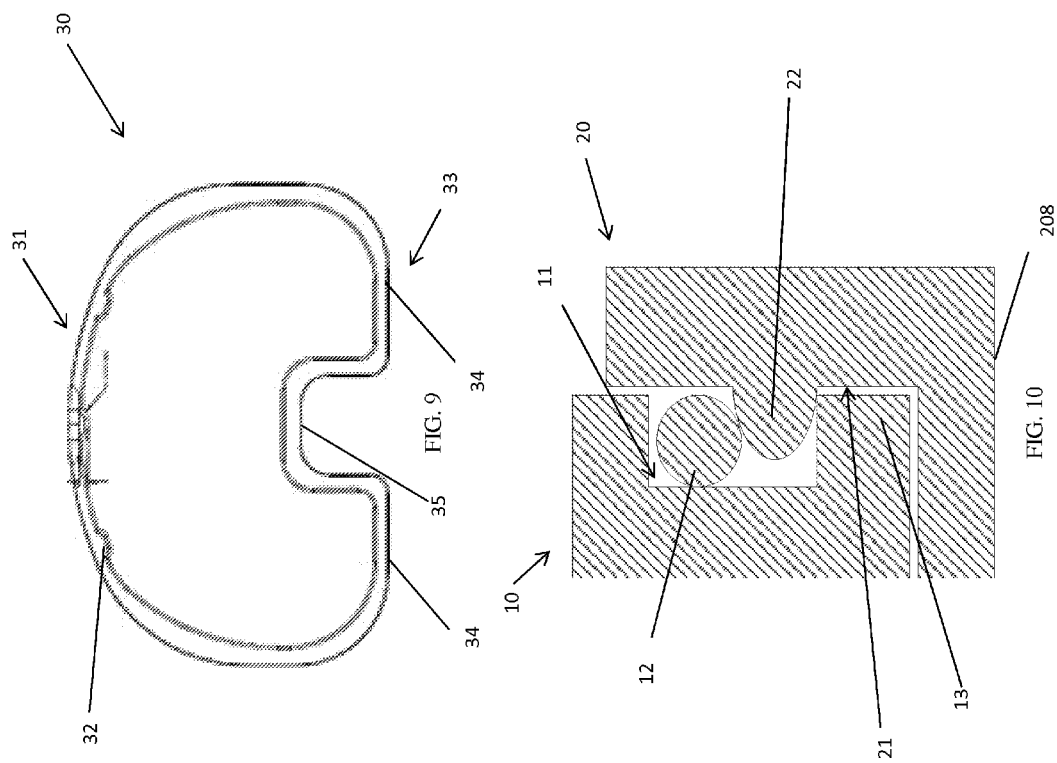

METHOD OF IMPROVING BOND STRENGTH OF POLYMERIC IMPLANTS WITH BONE CEMENT

BACKGROUND OF THE INVENTION

The present invention relates to an orthopedic prosthesis utilized in knee joint replacements. More particularly, the present invention is directed to a tibial implant system comprising a tibial insert and interchangeable tibial trays, one made of a metal and one made of a polymer.

Knee arthroplasty is a well-known surgical procedure to replace the weight-bearing surfaces of the knee joint to relieve pain and disability. It has enabled many individuals to function normally where it otherwise would be impossible. Artificial joints usually comprise metallic, ceramic, or plastic components implanted into existing bone.

In a typical procedure, a tibial tray or baseplate is mounted on a prepared proximal tibia of a patient and a tibial bearing insert is mounted on the tibial tray. Methods and corresponding tibial trays exist that allow for implantation into the tibia with or without the use of bone cement.

Earlier designs of tibial implant systems were typically composed primarily of metal trays or baseplates and bearings made of ultra-high-molecular-weight polyethylene (hereinafter "UHMWPE"). An earlier system, known as a monolithic UHMWPE device, comprised the bearing insert and bone-contacting portion as one piece implanted into the tibia through cement fixation. Although the system was resistant to stress shielding and had a long in vivo survival rate, the system fell out of favor with the medical industry because it was difficult to implant into the patient and because the bond between UHMWPE and bone with bone cement is not as strong as the bond with metal.

An improvement which is still currently used is a metal-backed UHMWPE modular tibia, which comprises a metal tray and a separate UHMWPE tibial insert. Although the two-part system made the device much easier to implant, the system was expensive.

Lastly, a system having a tibial tray composed of a polymer-porous metal composite has been recently developed for fixation without the need for bone cement, as can be seen in U.S. Pat. App. 2010/0100191, U.S. Pat. App. 2009/0084491, or U.S. Pat. App. 2011/0035018. Thus far, clinical results have shown that the cement-less bond is weaker than a bond using bone cement. In addition, devices comprising polymer-metal composites are expensive to manufacture.

Thus, there is a need for a modular tibial tray and insert system which can produce an improved, sustained bond with bone cement, reduces stress shielding, has improved resistance to fracture and wear, provides ease of use for surgeons, and be inexpensive to manufacture.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body. The term "sagittal" refers to the plane dividing the body into left and right halves. The term "coronal" refers to the plane dividing the body into front and back halves.

BRIEF SUMMARY OF THE INVENTION

Accordingly, one aspect of the present invention is to provide a tibial implant system comprising a polymeric tibial insert which can securely engage with a first or second tibial tray, albeit through differing connections at their respective anterior portions. The preferred embodiment of the tibial insert includes a locking wire mounted in an anterior recess, a locking tab along an anterior surface, and a locking tab disposed along a posterior surface. The first tibial tray comprises polymer, which in a preferred embodiment is polyether ether ketone (PEEK), and includes a bead formed along an anterior wall and an undercut area along a posterior wall. The second tibial tray comprises metal and includes a plurality of barbs along an anterior wall and an undercut area along a posterior wall. The metal tray is similar to those already in use and may be made of titanium, titanium alloy, cobalt chrome, molybdenum alloy, or stainless steel.

A further aspect of the present invention is to provide a method which improves the bond strength between a PEEK implant and bone cement, comprising the steps of loading a PEEK implant into a masking fixture, masking areas of the PEEK implant that will be subjected to high bending stresses, blasting a water soluble abrasive powder against the PEEK implant to achieve a certain average surface roughness, submerging the PEEK implant into water, and allowing the PEEK implant to air dry.

BRIEF DESCRIPTION OF THE DRAWINGS

FIG. 1 is a front view of a UHMWPE tibial bearing insert for the tibial trays according to the present invention;

FIG. 2 is a top view of the tibial insert of FIG. 1;

FIG. 3 is a cross-sectional side view of the tibial insert of FIG. 1 along line 3-3;

FIG. 4 is an enlarged view of detail A of the cross-sectional side view FIG. 3;

FIG. 5 is a top view of a polymeric tibial tray according to the present invention;

FIG. 6 is a front view of a metallic tibial tray according to the present invention;

FIG. 7 is a cross-sectional side view of the metallic tibial tray of FIG. 6 along line 7-7;

FIG. 8 is an enlarged view of detail B of the anterior wall of the metallic tibial tray of FIG. 7;

FIG. 9 is a top view of the metallic tibial tray of FIG. 6;

FIG. 10 is an enlarged schematic cross-sectional view of the engagement between the polyethylene tibial insert anterior surface and the polymeric tray anterior wall.

DETAILED DESCRIPTION

Figure 11:
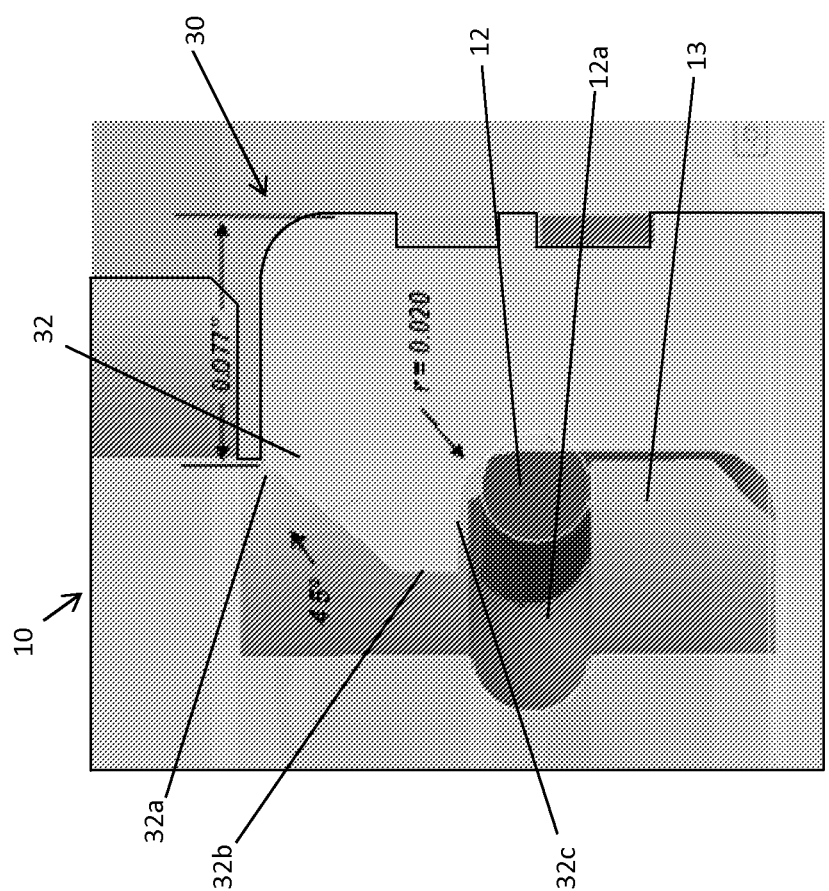
FIG. 11 is an enlarged cross-sectional view of the engagement between the polyethylene tibial insert anterior surface and the metallic tray anterior wall.

FIGS. 1 and 2 illustrate a representative UHMWPE tibial bearing insert according to the present invention, generally denoted as 10. The tibial insert 10 comprises an anterior surface 11 including a locking wire 12 and locking tab 13 and a posterior surface 14 including an intracondylar recess 18 and locking recesses 15, shown in FIG. 3 (not in FIG. 2). The insert also has a bearing surface 100. In an alternative embodiment, an additional locking recess 15 may be placed within the intracondylar recess 18. Locking recess 15 engages a protrusion 24a, 34a formed on the posterior surfaces 23, 33 of the tibial trays 20, 30 as shown in FIGS. 5 and 9.

FIGS. 3 and 4 illustrate a cross-sectional view of the tibial insert 10 along line 3-3 of FIG. 1. Referring to FIG. 3, the locking wire 12 is located above the locking tab 13 along the anterior surface 11, whereas the locking recess is disposed along the lower portion of the posterior surface 14.

FIG. 4 is an enlarged view of detail A of FIG. 3, showing the anterior surface 11 of the tibial insert 10, illustrating the placement of the locking wire 12 in a groove 12a formed above the locking tab 13. As shown, the locking wire 12 is disposed above the locking tab 13, with a space between the two parts. Furthermore, the locking wire 12 is disposed along a slot which allows the wire 12 to resiliently and posteriorly deflect into the groove 12a when a compressive force is applied during insertion of the insert 10 into the tray. Additionally, FIG. 3 shows a view of the posterior surface 14 including locking recess 15 and a flange 17 extending outwardly of the tray contacting surface 19.

FIG. 5 illustrates a representative polymeric tibial tray 20 according to the present invention. The polymeric tray 20 comprises an anterior wall 21 including a bead 22 running along an inner posteriorly facing surface of anterior wall 21 and a posterior wall 23 including undercuts 24 located below protrusion 24a and receiving flange portion 17 of the insert 10, and an intracondylar recess 25. Alternately the bead 22 can be discontinuously spaced along the wall 21 such as at the medial corner 21a and lateral corner 21c of the anterior surface 21 and optimally along the central anterior surface 21b. The polymeric tray 20 further comprises a keel 206 (not shown) which is implanted into the tibia and a bone contacting surface 208 (FIG. 10). An additional undercut 24 may also be placed within the intracondylar recess 25 for engaging a flange portion 17 located on the insert 10.

FIG. 6 illustrates a front view of a representative metallic tibial tray 30. The metallic tray 30 comprises an anterior wall 31 including a plurality of barbs 32 (FIGS. 7, 8, and 9), disposed alongside and protruding posteriorly, and a posterior wall 33 including undercuts 34 and an intracondylar recess 35 (FIG. 9). An additional undercut 34 may also be placed within the intracondylar recess 35 (FIG. 9). The metallic tray 30 further comprises a keel 306 which is implanted into the tibia and a bone contacting surface 308.

FIG. 7 illustrates a cross-sectional side view of the metallic tray 30 along line 7-7 of FIG. 6. As shown, the barbs 32 protrude posteriorly and run continuously along a substantial portion of the anterior wall 31. Furthermore, the intracondylar recess 35 is centrally disposed on a sagittal plane bisecting the posterior wall 33 with the undercuts 34 and protrusions 34a on the anteriorly facing surface of the posterior wall 33 (FIG. 9).

FIG. 8 is an enlarged view of detail B of FIG. 7, the anterior wall 31 of the metallic tray 30, illustrating the placement of the barbs 32 along the anterior wall 31. As shown, the barbs 32 include a chamfer 32a which extends posteriorly, a tip 32b, an underside 32c which faces distally, and a proximally facing surface 32d on which tibial insert 10 is mounted. The barbs 32 are placed along an upper portion of the anterior wall 31 so as to leave space below for insertion of the tibial bearing insert 10. Furthermore, the locking wire is sufficiently thin to be capable of resiliently deflecting in the anterior-posterior direction when a force is applied against it by the barbs 32 during insertion of the insert 10.

FIG. 9 is a top view of the metallic tibial tray 30 according to the present invention. As shown, a plurality of barbs 32 are disposed alongside the anterior wall 31 and extend posteriorly for engaging the anterior surface of the tibial insert 10. Furthermore, the posterior wall 33 includes undercuts 34, protrusions 34a, and an intracondylar recess 35. An additional undercut 34 and protrusion 34a may also be placed within the intracondylar recess 35. The posterior wall undercuts 24, 34 and protrusions 24a, 34a of the polymeric tray 20 and metallic tray 30 may be identical in design so that the same tibial insert 10 can be used in either tray.

FIG. 10 is an enlarged schematic cross-sectional side view along line 10-10 of FIG. 5 of the engagement between the tibial insert anterior surface 11 and the polymeric tray posterior surface of the anterior wall 21. The tibial insert is first engaged with the polymeric tray 20 through insertion of the flanges 17 into the posterior undercuts 24, wherein the protrusions 24a engage with the locking recesses (in FIG. 5). Afterwards, the insert anterior surface 11 is snap-fit into engagement with the tray anterior wall 21, wherein the locking tab 13 forces the anterior wall 21 to resiliently deflect anteriorly and snap posteriorly back into place with the bead 22 fitted between the locking wire 12 and locking tab 13. Accordingly, the bead 22 should be sufficiently sized to protrude past the locking wire 12 and the locking tab 13 when the tibial insert 10 is snap-fit into the polymeric tray 20. Thus, the tibial insert 10 is held in secure engagement with the polymeric tray 20 through connections at their posterior and anterior portions.

FIG. 11 is an enlarged cross-sectional side view of the engagement between the tibial insert anterior surface 11 and the metallic tray anterior wall 31. The tibial insert 10 is first engaged with the metallic tray 30 through insertion of the flanges 17 into the posterior undercuts 34, wherein the protrusions 34a engage with the locking recesses 15 (in FIG. 9). Afterwards, the insert anterior surface 11 is snap-fit into engagement with the tray anterior wall 31, wherein the plurality of barbs 32 forces the locking wire 12 to resiliently deflect posteriorly into the groove 12a and then snap anteriorly back into place underneath the barbs 32. Accordingly, for each barb 32, the chamfers 32a must be sufficiently angled to extend posteriorly past the locking wire 12 such that the tips 32b may push the wire 12 into the groove 12a and, upon the wire 12 snapping back into place, the undersides 32c may subsequently prevent the locking wire 12 from moving in an upward direction. Thus, the tibial insert 10 is held in secure engagement with the metallic tray 30 through connections at their posterior and anterior portions.

In a preferred embodiment of the present invention, the polymeric tray 20 is formed from polyether ether ketone (hereinafter "PEEK"), preferably PEEK with a crystallinity of less than 30 percent. Due to its relative inertness and nonporousness, PEEK biomaterials, including PAEK, have been found to be an attractive platform upon which to develop implants such as the present invention. Benefits include lower stiffness which results in reduced stress shielding, sustained bonding strength to bone cement in body fluid, reduced backside wear between the polymeric tray 20 and the tibial insert 10, ease of manufacture, and lower costs.

Furthermore, in the preferred embodiment, the polymeric tray's 20 bone-contacting surface 208 is grit-blasted to a high surface roughness in order to increase its initial bond strength with bone cement. Preferably, the blast media used is sodium bicarbonate or a water-soluble grit of similar hardness. The polymeric tray 20 is grit-blasted at a pressure between 105 and 110 PSI to a high surface roughness in order to enhance its initial bond strength with bone cement. The grit-blasting method comprises the steps of loading the tray into a masking fixture, masking areas of the tray that will be subjected to high bending stresses, blasting an abrasive powder against the tray to achieve an average surface roughness of between 4 and 6 micrometers, submerging the tray in water having a temperature between 60 and 70 degrees Celsius for 2 minutes, and allowing the tray to air dry.

In a preferred embodiment of the grit-blasting method, the grit-blasting machine is a suction-type or equivalent and has a 5/32 inch air jet and a nozzle having a 5/16 inch diameter orifice. The machine may be automated or manually operated. Furthermore, the preferred method includes focusing the nozzle perpendicular to the intended blasting area from a distance of 3 to 4 inches. If a perpendicular angle is impossible, the minimum allowable angle should be no less than 45 degrees. Blasting is continued until the desired surface roughness of 4 to 6 micrometers is reached.

Preferably, the blast media used is sodium bicarbonate or another abrasive nonmetal, water-soluble, and noncorrosive powder having a particle size of distribution of less than 10 percent 210 micrometer particles, less than 25 percent 270 micrometer particles, less than 50 percent 350 micrometer particles, less than 75 percent 430 micrometer particles, and less than 90 percent 510 micrometer particles. In addition, the grit-blasting technique is performed below the glass transition temperature of the polymer being roughened by the technique. Below the glass transition temperature polymers are more brittle than they are above their glass transition temperature. As a result, it is easier to create a roughened surface on a polymer when it is below its glass transition temperature. Accordingly, there is a disadvantage to creating a roughened polymeric surface by grit-blasting the mold into which a polymer material could be injected. As a consequence of both material flow inherent to the molding (injection or compression) process and the molding process taking place above the glass transition temperature, the surface roughness achieved by molding roughness into a part is generally not equivalent to the surface roughness achieved by grit-blasting the part after molding. It has been discovered that grit-blasted polymeric surfaces of a given roughness have better adhesion to bone cement than molded polymeric surface of the same roughness.

Thus, according to the invention, the tibial insert is shaped to lockingly engage with either the polymeric tibial tray 20 or the metallic tibial tray 30, albeit through differing means of engagement. During implementation, either the polymeric tray 20 or metallic tray 30 may be chosen for implantation into the resected tibia and receive the same UHMWPE bearing insert 10.

The interchangeability of a polymeric tray 20 or metallic tray 30 provides the option of choosing between implantation with or without the use of bone cement. Implementing the polymeric tray 20, particularly in the preferred embodiment in which the bone-contacting surface 208 is grit-blasted to a certain roughness, allows for a stronger bond with bone cement than metallic tibial trays. However, use of a metallic tray 30 would still be appropriate where bonding through cementless bone tissue ingrowth would be preferable to using bone cement. Because all cementless tibial trays are currently made of metal, a polymeric tray 20 which is compatible with an already-existing line of tibial inserts would reduce design and manufacturing costs and allow for the option of using bone cement without the need for a new tibial insert design.

In addition, the interchangeability of the present invention allows for consideration of a patient's bone stock. Polymeric trays are more flexible than their metallic counterparts and are therefore less likely to shield from stress areas of the bone where bone resorption has occurred with metallic trays. Thus, a younger patient with relatively strong bone stock would benefit from the loading pattern provided by a polymeric tray whereas a metallic tray would be more appropriate for an older patient with weaker bone stock. Thus, the compatibility of both types of tibial trays with the same tibial insert provides more options and increases design and manufacturing efficiency.

Lastly, the interchangeability between the polymeric and metallic trays would allow a provider to offer a more competitively priced implant system because a polymeric tray can be significantly less expensive to manufacture than a metallic tray. Thus, the company would be able to offer a less expensively priced polymeric tray in value markets while still being able to offer a metallic tray without having to design a different tibial insert for each tray.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for improving the bond between a molded PEEK joint component and bone cement, comprising:
    masking areas of the PEEK joint component that are subjected to high bending stress;
    thereafter roughening a surface of the molded PEEK joint component by air-blasting abrasive water-soluble particles against the PEEK component at a pressure between 105 and 110 PSI, and at a temperature less than the glass transition temperature of the PEEK until an average surface roughness of between 4 and 6 micrometers is attained;
    removing any residual abrasive water-soluble particles by submerging the PEEK component in water at a temperature of between 60 and 70 degrees Celsius for 2 to 3 minutes; and
    allowing the PEEK component to air dry;
    wherein 90 percent of the abrasive particles are less than 510 μm particles in size; and
    wherein the abrasive particles are nonmetal, water-soluble, and noncorrosive.

2. The method of claim 1, wherein the abrasive particles are sodium bicarbonate.

3. The method of claim 2, wherein no more than 75 percent of the particles are less than 430 μm in size.

4. The method of claim 3, wherein no more than 50 percent of the particles are less than 350 μm in size.

5. The method of claim 4, wherein no more than 25 percent of the particles are less than 270 μm in size.

6. The method of claim 5, wherein no more than 10 percent of the particles are less than 210 μm in size.

7. A method for improving the bond between a molded polymeric joint component and bone cement, comprising:
    masking areas of the PEEK joint component that are subjected to high bending stress;
    thereafter roughening a surface of the polymeric component by air-blasting abrasive water-soluble particles against the polymeric component at a pressure between 105 and 110 PSI, and a temperature less than the glass transition temperature of the polymer until an average surface roughness of between 4 and 6 micrometers is attained;
    removing any residual abrasive water-soluble particles by submerging the polymeric component in water at a temperature of between 60 and 70 degrees Celsius for 2 to 3 minutes; and
    allowing the polymeric component to air dry;
    wherein 90 percent of the abrasive particles are less than 510 μm particles in size; and
    wherein the abrasive particles are nonmetal, water-soluble, and noncorrosive.

8. The method of claim 7, wherein the abrasive particles are sodium bicarbonate.

9. The method of claim 8, wherein no more than 75 percent of the particles are less than 430 μm in size.

10. The method of claim 9, wherein no more than 50 percent of the particles are less than 350 μm in size.

11. The method of claim 10, wherein no more than 25 percent of the particles are less than 270 μm in size.

12. The method of claim 11, wherein no more than 10 percent of the particles are less than 210 μm in size.

* * * * *